United States Patent

Mastrorio et al.

[11] Patent Number: 5,746,272
[45] Date of Patent: May 5, 1998

[54] INVESTMENT CASTING

[75] Inventors: Brooke W. Mastrorio, Lakeville; Douglas A. Fifolt, South Easton, both of Mass.

[73] Assignee: Johnson & Johnson Professional, Inc., Raynham, Mass.

[21] Appl. No.: 724,732

[22] Filed: Sep. 30, 1996

[51] Int. Cl.$^6$ ..................... B22C 9/04
[52] U.S. Cl. .............. 164/516; 164/35; 164/45; 264/221
[58] Field of Search ............... 164/45, 34, 35, 164/516; 264/317, 221

[56] References Cited

U.S. PATENT DOCUMENTS

| | | | |
|---|---|---|---|
| 3,835,913 | 9/1974 | Vandemark et al. | 164/35 |
| 4,066,116 | 1/1978 | Blazek et al. | 164/17 |
| 4,109,699 | 8/1978 | Miller et al. | 164/244 |
| 4,355,428 | 10/1982 | Deloison et al. | 3/1.91 |
| 4,600,546 | 7/1986 | Grundei | 164/34 |
| 4,651,799 | 3/1987 | Chandley | 164/35 |
| 4,730,657 | 3/1988 | Carson et al. | 164/23 |
| 4,844,144 | 7/1989 | Murphy et al. | 164/35 |
| 5,007,931 | 4/1991 | Smith | 623/23 |
| 5,042,560 | 8/1991 | Ahlers | 164/45 |
| 5,069,271 | 12/1991 | Chandley et al. | 164/516 |
| 5,176,188 | 1/1993 | Quinn et al. | 164/516 |
| 5,204,055 | 4/1993 | Sachs et al. | 419/2 |
| 5,391,460 | 2/1995 | Dougherty et al. | 430/269 |

FOREIGN PATENT DOCUMENTS

| | | | |
|---|---|---|---|
| 63-194842 | 8/1988 | Japan | 164/35 |
| 63-212039 | 9/1988 | Japan | 164/35 |
| 360845 | 3/1991 | Japan . | |

OTHER PUBLICATIONS

*Alternative Methods for Custom Implant Production Utilizing a Combination of Rapid Prototyping Technology and Conventional Investment Casting*, B.A. Weeden, A.P. Sanders, D.S. LaSalle, G.P. Trottier, Johnson & Johnson Professional, Inc., 325 Paramount Drive, Raynham, MA 02767, USA, Mar. 31, 1996.

Primary Examiner—Kuang Y. Lin
Attorney, Agent, or Firm—Nutter, McClennen & Fish, LLP

[57] ABSTRACT

Methods are provided for producing investment cast articles, such as orthopedic implants, or portions thereof, having at least a partially textured surface that is formed during casting of the article. In an exemplary method, a textured metal casting is produced by creating a heat destructible pattern and spraying the pattern with a texturing material to cause the texturing material to form a textured surface on at least a portion of the pattern. In another embodiment, a textured template is pressed against a heat softenable pattern to provide a textured pattern. With respect to each of these methods, a shell is created around the textured pattern to form a mold, and the pattern is removed from the shell. Molten metal is introduced into the mold and allowed to harden, after which the mold is removed.

16 Claims, 1 Drawing Sheet

INVESTMENT CASTING

FIELD OF THE INVENTION

The present invention relates to investment casting, and more particularly to the manufacture of investment cast articles, such as orthopedic implants, with a textured surface.

BACKGROUND OF THE INVENTION

Various metal casting processes, such as investment (or "lost wax") casting are well known for the fabrication of metal objects. This process requires several steps, the first of which is to create or provide a pattern or shape to be replicated. The pattern, often made of wax, is used to make a mold that is then used to form cast metal articles.

Typically, several wax patterns are joined together on a wax "tree" to enable the simultaneous manufacture of several parts. The tree is a solid wax tube that has side walls to which a stem of each wax pattern is joined to form a cluster. The wax tree defines what will become a gate leading to passages for allowing molten metal to travel through the mold to each cluster and part pattern. Once all of the wax patterns are joined to the wax tree, the cluster is coated with one or more coats of a refractory by dipping the wax pattern-tree assembly in a ceramic slurry. After the slurry dries, fabrication of a shell or mold is completed by heating the slurry coated wax to cure or harden the ceramic, and to melt out the solid wax patterns and the wax tree. Molten metal is then poured into the shell so that it fills each of the cavities formerly occupied by the wax patterns and the wax tree. After the metal has cooled and hardened, the shell is fractured and removed, and the cast metal parts are severed from the metal tree. The cast parts are then subjected to post-machining, grinding off the gates, bead blasting, and polishing, as required.

With respect to medical implants, such as joint prosthesis components, it has been discovered that texturing or roughening the surface of a cast metal implant can improve the interface and fixation between the implant and the bone, with or without bone cement. The creation of a roughened surface on an implant, whether it was investment cast or forged, is typically one of the last steps in the manufacturing process of the component. Known methods for obtaining a roughened surface include grit-blasting, grinding, direct machining, laser etching, and sintering of beads to the surface of the implant.

Known surface texturing techniques, however, have severe short-comings with respect to manufacturing speed, efficiency, and cost, as well as structural limitations and deficiencies. For example, if the surface of the implant is improperly roughened, the near finished implant must be discarded. Depending on the alloy used to fabricate the implant and the size of the implant, the creation of unacceptable texturing can significantly increase manufacturing cost. The creation of a textured surface requires a skilled craftsperson. Therefore, for other than simple, uniform texturing, precise replication of a particular configuration is difficult to achieve in even limited production quantities. Furthermore, known surface texturing techniques are incapable of creating certain complex shapes and patterns, such as undercutting, which foster bone ingrowth and more secure fixation. Yet another disadvantage of known techniques for texturing a previously-cast implant is that the application of texturing materials, such as with a plasma-spray process results in an imperfect bond between the sprayed-on material and the implant which can lead to abrasive detachment and weak substrate coating interfaces. Similarly, sintering beads on a surface causes loss of favorable mechanical properties.

SUMMARY OF THE INVENTION

The present invention overcomes the disadvantages of known surface texturing techniques by providing a heat destructible pattern having a textured surface. The textured pattern is used to create an investment casting mold which in turn is used to create the cast article. This technique allows very specific and/or complex patterns to be integrally formed with the implant surface as cast.

In an exemplary method, a textured metal casting, such as an orthopedic implant or a component thereof, is produced by creating a heat destructible pattern and spraying the pattern with a texturing material to cause the texturing material to form a textured surface on at least a portion of the pattern. The texturing material can include molten wax droplets that adhere to and/or melt at least a portion of the surface of the pattern or solid particles that adhere to and/or indent the surface of the pattern. The texturing material can be evenly or unevenly sprayed against the pattern at a selected temperature and velocity to create a desired texture. A shell is created around the textured pattern to form a mold, and the pattern is removed from the mold. Molten metal is introduced into the mold and allowed to harden, after which the mold is removed from the textured casting.

In another embodiment, a textured template is pressed against a heat softenable pattern to provide a textured pattern. The textured template can be formed by creating a data file that defines a three-dimensional textured template; providing the data file to a rapid prototyping machine; and forming a model representative of the three-dimensional textured template with the rapid prototyping machine. A second textured template can be provided that has a different texture than the first textured template.

BRIEF DESCRIPTION OF THE DRAWINGS

A more complete understanding of the present invention and the attendant advantages and features thereof will be more readily understood by reference to the following detailed description when it is considered in conjunction with the accompanying drawings wherein.

DETAILED DESCRIPTION OF THE INVENTION

A first embodiment of a method of making a textured investment casting begins with the step of creating a custom heat destructible pattern or selecting an existing pattern from stock supplies. Typically, patterns are made of investment casting wax, however, many plastics are also acceptable, as are hybrid wax/plastic patterns. As used herein, a "pattern" is full-scale representation or model of any article that is either machine or hand made. Exemplary patterns include components for orthopedic implants and portions thereof.

After the pattern is selected or created, a heat destructible texturing material is selected for spraying against the pattern. Exemplary texturing materials include wax droplets or beads that are molten, soft, or hard, and plastic particles or beads. However, any material which may be applied to the pattern and which will subsequently burn out of a mold cleanly may be used. As used herein, "particle" or "droplet" is intended to encompass any size or shape configuration obtainable with a given texturing material, and the particular size and configuration or morphology of a selected particle or droplet is selected to achieve a desired texture.

Figure 1:
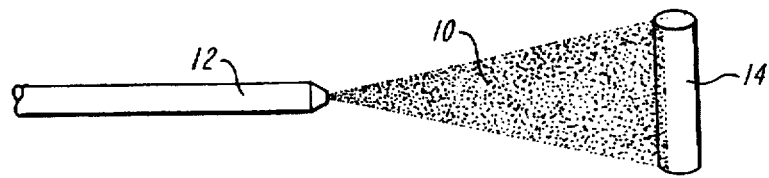
FIG. 1 is a simplified illustration of a pattern being sprayed with a texturing material.

Following selection of a texturing material, a spray is created with the texturing material and it is directed toward the pattern or the pattern is placed in the path of the spray. As used herein, a "spray" is intended to encompass everything from a concentrated, narrow stream to a diffuse mist, and "spray" should be broadly construed to mean placing the texturing material or a portion thereof in motion. The particular dispersion, concentration, temperature, and pressure of the spray are determined by the texturing material and the desired texture for the pattern. As illustrated in FIG. 1, molten wax or solid particles 10, such as wax or plastic beads under pressure can be ejected from a nozzle 12 to create a spray. A pattern 14 is shown in the path of the spray.

Figure 2:
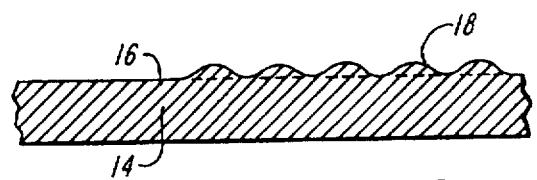
FIG. 2 is a sectional view of a portion of a pattern having wax spray texturing to create positive relief features.

FIG. 2 illustrates a pattern 14 that has been sprayed by molten wax droplets, wherein the molten wax temperature and spray velocity were such that at least some of the molten wax droplets adhered to at least a portion of the surface 16 of the pattern to create surface texturing, roughness, or bas relief. In FIG. 2, the droplets have been deposited to form bumps that can be defined as positive surface relief features, on a portion of the pattern surface 16.

Figure 3:
FIG. 3 is a sectional view of a portion of a pattern having wax spray texturing to create negative relief features.

FIG. 3 illustrates a pattern 14 that has been sprayed by molten wax droplets, wherein the molten wax temperature and spray velocity were such that at least some of the molten wax droplets melted away at least a portion of the surface 16 of the pattern to create surface texturing, roughness, or bas relief. In FIG. 3, the droplets have been created depressions, voids, or indentations 20 that can be defined as negative surface relief features, on a portion of the pattern surface 16.

The temperature of the spray of molten wax can be regulated to create positive and negative surface features in the same surface areas. Also, the spray of texturing material can be directed toward the pattern 16, or a portion thereof, to evenly or unevenly distribute the spray to create, respectively, a substantially uniform or irregular pattern. Furthermore, although the bumps 18 and indentions 20 appear rounded in the illustrations, their shapes can range from circular to linear, and the bumps and indentations can have angled or convoluted boundaries.

Figure 4:
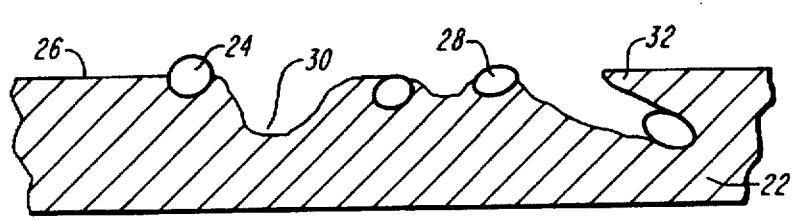
FIG. 4 is a sectional view of a portion of a pattern having solid particle texturing.

FIG. 4 illustrates a pattern 22 that has been sprayed by solid particles 24, wherein the particle temperature, spray velocity, and particle morphology were such that at least some of the particles adhered to at least a portion of the surface 26 of the pattern 22 to create surface texturing, roughness, or bas relief. The particles 24 form bumps 28 that can be defined as positive surface relief features, on a portion of the pattern surface 26. The particles can range from being barely to fully impacted in the surface of the pattern. Bumps are also created by the displacement of pattern material in response to particle impact.

FIG. 4 also illustrates additional surface texturing, roughness, or bas relief in the form of depressions, voids, or indentations 30 that can be defined as negative surface relief features. These indentations are created by impact of the particles 24 with the surface 26 and then bouncing off or not adhering to the surface. As with respect to the molten wax spray technique, the temperature of the particulate spray can be regulated to create positive and negative surface features in the same surface areas. Similarly, the particulate spray of texturing material can be directed toward the pattern 22, or a portion thereof, to evenly or unevenly distribute the spray to create, respectively, a substantially uniform or irregular pattern. Furthermore, although the bumps 28 and indentions 30 appear rounded in the illustrations, their shapes can range from circular to linear, and have angled or convoluted boundaries. If the particles impact the surface at an angle, an under-cut surface 32 is created.

Figure 5:
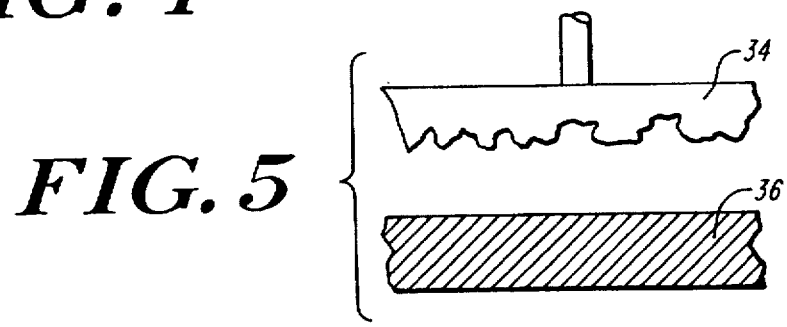
FIG. 5 is a schematic view of a pattern being textured with a template.

Yet another technique for creating a textured pattern includes pressing a textured template 34 against at least a portion of a heat softenable pattern 36 to provide a textured pattern, as shown in FIG. 5. Either the textured template 34, the pattern 36, or both can be heated to facilitate pattern creation. Alternatively, the template can create a texture on the pattern by pressing the template against the pattern with enough pressure to deform the pattern. This technique is well suited for applications requiring a precise and/or complicated pattern geometry, and it is particularly well suited for providing a texture that promotes bone ingrowth.

In an exemplary embodiment, the template 34 is a metal object fabricated using any known technique for creating a metal object. Alternatively, the template 34 can be fabricated from a plastic that has a higher melting/distortion point than the wax pattern. However, in other embodiments, the template is created with a rapid prototyping machine. The object created by the rapid prototyping machine can itself be used as the textured template, or it can be used as a model for the creation of an investment casting mold.

For example, a textured template can be provided by creating a data file that defines a three-dimensional textured template, wherein the textured template includes a texture pattern configured to promote bone ingrowth. The data file is provided to a rapid prototyping machine capable of creating a heat destructible model. A heat destructible model representative of the three-dimensional textured template is then created with the rapid prototyping machine. A heat resistant shell is formed around the heat destructible model and heat is applied to the shell to remove the heat destructible model therefrom. Molten metal is poured into the shell; the molten metal hardens; and the shell is removed. The thus formed textured template is heat pressed against at least a portion of the pattern to provide a textured pattern. A second textured template having a different texture than the first textured template can be provided and pressed on at least a portion of the pattern to provide a pattern with different textures on different regions thereof.

Having been imparted with a surface texture, the pattern, created by whatever method, is used to create a mold. In an exemplary method, the pattern is coated with particles of a refractory material by spraying or dipping to create a shell around the textured pattern. The textured pattern is removed from the shell by the application of heat which causes the pattern, and any blast media impacted thereon, to melt, burn, or vaporize, allowing it to be drained or exhausted from an opening in the shell. Heating, either in this or a subsequent step, cures the refractory material to complete the mold making process.

Subsequent casting steps are not discussed in great detail, as they are well known to those skilled in the art of metal casting. These steps include introducing molten metal, such as Cr-Co-Mo alloy (ASTM F75) through one or more gates in the mold. The mold and the metal are allowed to cool, and the mold is removed from the hardened metal. The textured implant can then be subjected to post-machining, grinding off of gates, bead blasting, and polishing, as required.

Each of the above techniques provides different manufacturing advantages. However, should a problem be encountered in the texturing steps, the cost associated with scrap is greatly reduced as only inexpensive wax is sacrificed rather than a nearly finished product. Accidentally roughened surfaces are easily smoothed by heating the wax.

Although the invention has been shown and described with respect to exemplary embodiments thereof, various other changes, omissions and additions in form and detail thereof may be made therein without departing from the spirit and scope of the invention.

What is claimed is:

1. A method of making a textured metal casting comprising the steps of:
   providing a heat destructible pattern having a substantially smooth surface region that is free of open pores;
   providing a heat destructible texturing material;
   creating a spray with the texturing material;
   directing the spray of the texturing material toward the substantially smooth surface region that is free of open pores to cause the texturing material to create a surface region that is no longer substantially smooth, thereby providing a textured pattern;
   creating a shell around the textured pattern;
   removing the textured pattern from the shell;
   introducing molten metal into the shell;
   allowing the molten metal to harden; and
   removing the shell from the hardened metal.

2. The method of claim 1, wherein the pattern includes a wax representation of at least a portion of an orthopedic implant.

3. The method of claim 2, wherein the texturing material includes wax.

4. The method of claim 3, wherein the step of creating a spray includes the step of producing a stream of molten wax droplets.

5. The method of claim 4, wherein the step of creating a spray includes the step of selecting a molten wax temperature and spray velocity such that at least some of the molten wax droplets adhere to at least a portion of the surface of the pattern.

6. The method of claim 4, wherein the step of creating a spray includes the step of selecting a molten wax temperature and spray velocity such that at least some of the molten wax droplets create an indentation in at least a portion of the surface of the pattern.

7. The method of claim 4, wherein the step of creating a spray includes the step of selecting a molten wax temperature and spray velocity such that at least some of the molten wax droplets create indentations in at least a portion of the surface of the pattern and at least some of the molten wax droplets adhere to at least a portion of the surface of the pattern.

8. The method of claim 2, wherein the texturing material includes solid particles.

9. The method of claim 8, wherein the solid particles include wax beads.

10. The method of claim 8, wherein the solid particles include plastic.

11. The method of claim 8, wherein the step of creating a spray includes the step of producing a stream of solid particles.

12. The method of claim 11, wherein the step of creating a spray includes the step of selecting a solid particle morphology and spray velocity such that at least some of the solid particles adhere to at least a portion of the pattern.

13. The method of claim 11, wherein the step of creating a spray includes the step of selecting a solid particle morphology and spray velocity such that at least some of the solid particles indent at least a portion of the surface of the pattern and do not adhere thereto.

14. The method of claim 11, wherein the step of creating a spray includes the step of selecting a solid particle morphology and spray velocity such that at least some of the solid particles indent at least a portion of the surface of the pattern without adhering thereto, and at least some of the solid particles adhere to at least a portion of the surface of the pattern.

15. A method of making a textured orthopedic implant comprising the steps of:
    creating a wax pattern having the shape and size of a selected orthopedic implant and having a substantially smooth surface region that is free of open pores;
    providing a heat destructible texturing material including wax;
    creating a spray with the texturing material by producing a stream of molten wax droplets at a selected temperature and spray velocity;
    directing the spray of the molten wax droplets toward the wax pattern such that at least some of the molten wax droplets adhere to at least a portion of the substantially smooth surface region of the wax pattern to create a lumpy surface region;
    creating a shell around the textured pattern;
    removing the textured pattern from the shell;
    introducing molten metal into the shell;
    allowing the molten metal to harden; and
    removing the shell from the hardened metal.

16. A method of making a textured orthopedic implant comprising the steps of:
    creating a heat destructible pattern representative of an orthopedic implant and having a substantially smooth surface region that is free of open pores;
    providing a heat destructible texturing material including solid particles;
    creating a spray with the texturing material by placing a stream of solid particles at a selected temperature in motion at a selected velocity;
    directing the stream of the solid particles toward the substantially smooth surface region of the pattern such that at least some of the solid particles indent at least a portion of the surface of the pattern without adhering thereto, and at least some of the solid particles adhere to at least a portion of the surface of the pattern to create a lumpy surface region;
    creating a shell around the textured pattern;
    removing the textured pattern from the shell;
    introducing molten metal into the shell;
    allowing the molten metal to harden; and
    removing the shell from the hardened metal.

* * * * *